US009493583B2

(12) United States Patent
Charvet et al.

(10) Patent No.: US 9,493,583 B2
(45) Date of Patent: *Nov. 15, 2016

(54) ANIONIC POLYSACCHARIDES FUNCTIONALIZED BY A HYDROPHOBIC ACID DERIVATIVE

(75) Inventors: Richard Charvet, Rillieux la Pape (FR); Remi Soula, Lyons (FR); Olivier Soula, Meyzieu (FR)

(73) Assignee: ADOCIA, Lyons (FR)

(*) Notice: Subject to any disclaimer, the term of this patent is extended or adjusted under 35 U.S.C. 154(b) by 1632 days.

This patent is subject to a terminal disclaimer.

(21) Appl. No.: 12/977,690

(22) Filed: Dec. 23, 2010

(65) Prior Publication Data

US 2011/0172166 A1 Jul. 14, 2011

Related U.S. Application Data

(63) Continuation of application No. PCT/IB2009/007899, filed on Dec. 23, 2009.

(60) Provisional application No. 61/282,836, filed on Apr. 7, 2010.

(30) Foreign Application Priority Data

Apr. 7, 2010 (FR) ..................................... 10 01439

(51) Int. Cl.
| | |
|---|---|
| *A61K 6/00* | (2006.01) |
| *C08B 37/02* | (2006.01) |
| *A61K 47/36* | (2006.01) |
| *C08B 1/00* | (2006.01) |
| *C08B 37/00* | (2006.01) |
| *C08B 37/08* | (2006.01) |

(52) U.S. Cl.
CPC ........... *C08B 37/0021* (2013.01); *A61K 47/36* (2013.01); *C08B 1/00* (2013.01); *C08B 37/0006* (2013.01); *C08B 37/006* (2013.01); *C08B 37/0009* (2013.01); *C08B 37/0018* (2013.01); *C08B 37/0024* (2013.01); *C08B 37/0045* (2013.01); *C08B 37/0054* (2013.01); *C08B 37/0057* (2013.01); *C08B 37/0072* (2013.01); *C08B 37/0084* (2013.01)

(58) Field of Classification Search
None
See application file for complete search history.

(56) References Cited

U.S. PATENT DOCUMENTS

| | | | |
|---|---|---|---|
| 2,387,201 | A | 10/1945 | Weiner |
| 2,954,372 | A | 9/1960 | Novak |
| 4,826,818 | A | 5/1989 | Mori et al. |
| 5,208,146 | A | 5/1993 | Irie |
| 6,656,481 | B1 | 12/2003 | Shiku et al. |

| | | | |
|---|---|---|---|
| 2006/0153846 | A1 | 7/2006 | Krause et al. |
| 2007/0142324 | A1* | 6/2007 | Perly et al. ...................... 514/58 |
| 2008/0014250 | A1* | 1/2008 | Soula et al. .................. 424/443 |

FOREIGN PATENT DOCUMENTS

| | | |
|---|---|---|
| CN | 1401389 A | 3/2003 |
| EP | 0 792 888 A1 | 9/1997 |
| EP | 1 475 100 A1 | 11/2004 |
| EP | 1475100 A1 * | 11/2004 |
| EP | 1 493 754 A1 | 1/2005 |
| NZ | 534542 | 12/2008 |
| WO | WO 01/14881 A1 | 3/2001 |
| WO | WO 02/096457 A2 | 12/2002 |
| WO | WO 02/096457 A3 | 12/2002 |
| WO | WO 2006/044908 A2 | 4/2006 |
| WO | WO 2006 106 521 A2 | 10/2006 |
| WO | WO 2006/106521 A3 | 10/2006 |
| WO | WO 2007034320 A2 * | 3/2007 |
| WO | WO 2007/116143 A1 | 10/2007 |
| WO | WO 2007/147001 A2 | 12/2007 |
| WO | WO 2007/147001 A3 | 12/2007 |
| WO | WO 2008/038111 A1 | 4/2008 |
| WO | WO 2008/121615 A2 | 10/2008 |
| WO | WO 2009/127940 A1 | 10/2009 |

OTHER PUBLICATIONS

French Patent Office, French Search Report for FR 1001439 (with English translation), dated Nov. 22, 2010, pp. 1-2.
Morooka et al., "Dielectric Properties of Cellulose Acylates," Journal of Applied Polymer Science, 1984, pp. 3981-3990, vol. 29; John Wiley & Sons, Inc.
Aburto et al., "Synthesis, Characterization, and Biodegradability of Fatty-Acid Esters of Amylose and Starch," Journal of Applied Polymer Science, 1999, pp. 1440-1451, vol. 74; John Wiley & Sons, Inc.
Nichifor et al., "Bile acids covalently bound to polysaccharides 1. Esters of bile acids with dextran," European Polymer Journal, 1999, pp. 2125-2129, vol. 35; Elsevier Science Ltd.
Laletin et al., Vysokomol Soedin Ser A, 1968, pp. 652-656, vol. 10, No. 3.
Heinze et al., "Unconventional cellulose esters: synthesis, characterization and structure-property relations," Cellulose, 2003, pp. 283-296, vol. 10; Kluwer Academic Publishers, Netherlands.
Pal et al., "Molecular mechanism of physical gelation of hydrocarbons by fatty acid amides of natural amino acids," Tetrahedron, 2007, pp. 7334-7348, vol. 63; Elsevier Ltd.
Paul et al., "N, N-Carbonyldiimidazole in Peptide Synthesis. III. A synthesis of Iso-leucine-5 Angiotensin II Amide-1," Journal of Organic Chemistry, 1962, pp. 2094-2099, vol. 27.

(Continued)

*Primary Examiner* — Jeanette Lieb
(74) *Attorney, Agent, or Firm* — Oliff PLC

(57) ABSTRACT

A novel anionic polysaccharides functionalized by at least one hydrophobic acid derivative. These novel anionic polysaccharides including hydrophobic groups have good biocompatibility and their hydrophobicity can be easily adjusted without detrimentally affecting the biocompatibility or the stability. A method of synthesis which makes it possible to produce them and to pharmaceutical compositions including them.

44 Claims, No Drawings

(56) References Cited

OTHER PUBLICATIONS

Dale et al., "The Process Development of a Scaleable Route to the PDE5 Inhibitor UK-357,903," Organic Process Research & Development, 2002, pp. 767-772, vol. 6, No. 2; American Chemical Society.

Sanchez-Chaves et al., "Poly (vinyl alcohol) functionalized by monosuccinate groups. Coupling of bioactive amino compounds," Polymer, 1998, pp. 2751-2757, vol. 39, No. 13; Elsevier Science Ltd.

Knockler et al., "Isocynates, Part 4. Convenient Phosgene-Free Method for the Synthesis and Derivatization of Enantiopure α-Isocyanato Carboxylic Acid Esters," Synlett, 1997, pp. 925-928.

Sawant et al., "'Smart' Drug Delivery Systems: Double-Targeted pH-Responsive Pharmaceutical Nanocarriers," 2006, pp. 943-949, vol. 17; American Chemical Society.

Morita et al., "Water-solvent method for tosylation and mesylation of primary alcohols promoted by KOH and catalytic amines," European Polymer Journal, 2005, pp. 711-715, vol. 7; Green Chemistry.

Co-pending U.S. Appl. No. 12/654,552, filed Dec. 23, 2009.

French Patent Office, International Search Report for PCT/IB2009/007899 (with English translation), dated Mar. 23, 2010, pp. 1-4 (1-3 for translation).

Crepona, et al. "Enzymatic degradation and immunogenic properties of derivatized dextrans," Biomaterials, Aug. 1991, pp. 550-554, vol. 12, No. 6.

Jun. 17, 2009 Search Report issued in French Application No. 0807438 (with translation).

Jun. 23, 2011 Written Opinion issued in Application No. PCT/IB2009/007899 (with translation).

Jul. 15, 2011 Office Action issued in U.S. Appl. No. 12/654,552.

Dec. 9, 2011 Office Action issued in U.S. Appl. No. 12/654,552.

\* cited by examiner

ANIONIC POLYSACCHARIDES FUNCTIONALIZED BY A HYDROPHOBIC ACID DERIVATIVE

This is a Continuation of International Application No. PCT/IB2009/007899 filed Dec. 23, 2009, and also claims the benefit of U.S. Provisional Application No. 61/282,836, filed Apr. 7, 2010 and French Patent Application No. 10/01439, filed Apr. 7, 2010.

The present invention relates to novel biocompatible polymers based on anionic polysaccharides functionalized by a hydrophobic acid derivative which can be of use in particular for the administration of active principle(s) (AP) to man or to animals for a therapeutic and/or prophylactic purpose.

Anionic polysaccharides functionalized by a hydrophobic acid derivative are, due to their structure and their biocompatibility, particularly advantageous in the pharmaceutical field and more particularly the field of the stabilization of protein active principles by the formation of complexes.

Hydrophobic acids are advantageous in the formulation of pharmaceutical active principles, in particular, due to their hydrophobic nature making it possible to adjust the hydrophobicity of the polymers onto which they may be grafted.

Their biocompatibility is excellent insofar as they play a role in numerous biochemical processes and are present in esterified form in the majority of tissues.

Techniques are known for grafting hydrophobic acids directly to the hydroxyl functions of dextran. These techniques result in the formation of a hydrophobic acid ester directly on the backbone of the polysaccharide. This has been carried out with activated derivatives of fatty acids, such as anhydrides (Novak L. J. and Tyree J. T. (1960), U.S. Pat. No. 2,954,372; Moorooka, T. et al., J. Appl. Polym. Sci., 1984, 29, 3981-3990), acyl chlorides (Ehrhardt S. et al. (1997), EP 792 888; Aburto, J. et al., J. Appl. Polym. Sci., 1999, 74, 1440-1451), N-acylureas (Nichifor, Marieta et al., Eur. Polym. J., 1999, 35, 2125-2129), and the like. Hydrophobic acids have also been grafted by transesterification starting from their ester derivatives (Laletin, A. J. et al., Vysokomol Soedin Ser A, 1968, 10, 652) and by activation techniques with tosyl chloride for example (Heinze, T. et al., Cellulose 2003, 10, 283-296). These methods have only been employed with neutral polysaccharides since they are not compatible with the presence of carboxylate functions on the polysaccharide.

The present invention relates to novel anionic polysaccharides functionalized by at least one hydrophobic acid derivative. These novel anionic polysaccharides comprising hydrophobic groups have good biocompatibility and their hydrophobicity can be easily adjusted without detrimentally affecting the biocompatibility or the stability.

It also relates to a method of synthesis which makes it possible to solve the abovementioned problems of synthesis. This method has made it possible to obtain anionic polysaccharides functionalized by hydrophobic acids.

The invention thus relates to anionic polysaccharides chosen from polysaccharides comprising carboxyl functions of formula I, said polysaccharides being monofunctionalized:

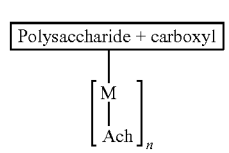

Formula I in which n represents the degree of functionalization of the saccharide units of the polysaccharide by -M-Ach and is between 0.01 and 0.7, M being:
either a sequence denoted —$F_1$—$R_1$-G comprising a connecting arm $R_1$ said connecting arm $R_1$ being bonded to the poly-saccharide via a bond $F_1$ resulting from the coupling between a reactive function of the precursor of the connecting arm $R_1$' and and a carboxyl function of the anionic polysaccharide and said hydrophobic radical (Ach) being bonded to the connecting arm $R_1$ via a function G resulting from the coupling between the acid function of the hydrophobic acid and a reactive function of the precursor of the connecting arm $R_1$', or a sequence denoted —$F_2$—$R_2$-G comprising a connecting arm $R_2$, said connecting arm $R_2$ being bonded to the polysaccharide via a bond $F_2$ resulting from the coupling between a reactive function of the precursor of the connecting arm $R_2$' and a hydroxyl function of the anionic polysaccharide and said hydrophobic radical (Ach) being bonded to the connecting arm $R_2$ via a function G resulting from the coupling between the acid function of the hydrophobic acid and a reactive function of the precursor of the linking arm $R_2$', $F_1$ being either an amide function or an ester function or a thioester function, F2 being a carbamate function, the unfunctionalized carboxyl functions of the anionic polysaccharide being in the cation carboxylate form, the cation preferably being that of an alkali metal, such as $Na^+$ or $K^+$, G being either an amide function or an ester function or a thioester function Ach being a radical resulting from the coupling between the acid function of a hydrophobic acid and a reactive function of the precursor of the connecting arm $R_1$' or $R_2$', Ach being composed of a chain comprising between 4 and 50 carbons which is optionally branched and/or unsaturated, which optionally comprises one or more heteroatoms, such as O, N and/or 5, and which optionally comprises one or more saturated, unsaturated or aromatic rings or heterocycles, $R_1$ being a divalent radical composed of a chain comprising between 1 and 15 carbons which is optionally branched and/or unsaturated, which optionally comprises one or more heteroatoms, such as O, N and/or S, and which optionally comprises one or more saturated, unsaturated or aromatic rings or heterocycles and resulting from the reaction of a precursor $R_1$' having at least two identical or different reactive functions chosen from the group consisting of alcohol, amine and thiol functions, R2 being a divalent radical composed of a chain comprising between 1 and 15 carbons which is optionally branched and/or unsaturated, which optionally comprises one or more heteroatoms, such as O, N and/or S, and which optionally comprises one or more saturated, unsaturated or aromatic rings or heterocycles and resulting from the reaction of a precursor R2' having at least two reactive functions, one being an amine and the other being chosen from the group consisting of alcohol, amine and thiol functions.

In one embodiment, the precursors $R_1$' and $R_2$' comprise an additional reactive function which is not functionalized.

When the unfunctionalized reactive function is an acid function, it is in the cation carboxylate form, the cation preferably being that of an alkali metal.

When the unfunctionalized reactive function is an amine function, it is in the form of an anion salt, the anion preferably being a halide.

In one embodiment, n is between 0.02 and 0.6.
In one embodiment, n is between 0.05 and 0.5.
In one embodiment, n is between 0.1 and 0.4.

The term "anionic" is understood to mean a polysaccharide which comprises unfunctionalized and salifiable carboxyl functions.

The term "monofunctionalized" is understood to mean an anionic polysaccharide which is functionalized by a single hydrophobic group and which does not comprise other substituents.

The term "degree of functionalization" is understood to mean the number of M-Ach functions per saccharide unit or, in other words, the total number of M-Ach functions with respect to the total number of saccharide units. This notion can also be expressed as molar fraction of the hydroxyl functions of the polysaccharide functionalized by M-Ach.

The term "degree of conversion" is understood to mean the number of hydroxyl functions converted to carboxylates per saccharide unit or, in other words, the total number of hydroxyl functions converted to carboxylates with respect to the total number of saccharide units. This notion can also be expressed as molar fraction. For example, polysaccharides for which the degree of conversion of the hydroxyl functions to carboxylates per saccharide unit is equal to or greater than 0.15 are polysaccharides for which at least 15 carboxyl functions per 100 saccharide units have been grafted.

The term "degree of polymerization m" is understood to mean the mean number of repeat units (monomers) per polymer chain. It is calculated by dividing the number-average molar mass by the mean weight of the repeat unit.

The term "number-average molar mass ($M_n$)" is understood to mean the arithmetic mean of the weights of each of the polymer chains. Thus, for a number $n_i$ of chains i with the molar mass $M_i$, $M_n = (\Sigma_i n_i M_i)/(\Sigma_i n_i)$.

The weight-average molar mass ($M_w$) is obtained with $M_w = (\Sigma_i n_i M_i^2)/(\Sigma_i n_i M_i)$, $n_i$ being the number of chains of polymer i with the molar mass $M_i$.

The polymers can also be characterized by the distribution of chain lengths, also known as polydispersity index (PI), which is equal to $M_w$ divided by $M_n$.

In one embodiment, the anionic polysaccharides are polysaccharides which naturally carry carboxyl functions and are chosen from the group consisting of alginate, hyaluronan and galacturonan.

In one embodiment, the anionic polysaccharides are synthetic polysaccharides obtained from polysaccharides naturally comprising carboxyl functions or from neutral polysaccharides, for which the degree of conversion of the hydroxyl functions to carboxylates per saccharide unit is equal to or greater than 0.15, of general formula II, $$\text{Polysaccharide} - \left[ \begin{array}{c} L \\ | \\ Q \end{array} \right]_i \qquad \text{Formula II}$$

the natural polysaccharides being chosen from the group of the polysaccharides predominantly composed of monomers bonded via glycoside bonds of (1,6) and/or (1,4) and/or (1,3) and/or (1,2) type, L being a bond resulting from the coupling between a precursor of the connecting arm Q and an —OH function of the polysaccharide and being either an ester, carbamate or ether function, i represents the degree of conversion of the hydroxyl functions to L-Q sequences per saccharide unit of the polysaccharide, Q being chosen from the radicals of general formula III:

$$-(CH_2)_a-\underset{R_4}{\overset{R_3}{C}}_b-(CH_2)_c-COOH \qquad \text{Formula III}$$

in which:
$1 \leq a+b+c \leq 6$, $0 \leq a \leq 3$, $0 \leq b \leq 3$ and $0 \leq c \leq 3$, $R_3$ and $R_4$, which are identical or different, are chosen from the group consisting of —H, linear or branched $C_1$ to $C_3$ alkyl, —COOH and the radical $$-(\underset{R'_4}{\overset{R'_3}{C}})_d-COOH \qquad \text{Formula IV}$$

of general formula IV in which:
$1 \leq d \leq 3$ and $R'_3$ and $R'_4$, which are identical or different, are chosen from the group consisting of —H and a linear or branched $C_1$ to $C_3$ alkyl group.

In one embodiment, $a+b+c \leq 5$
In one embodiment, $a+b+c \leq 4$.
In one embodiment, i is between 0.15 and 3.
In one embodiment, i is between 0.3 and 25.
In one embodiment, i is between 0.5 and 1.7.
In one embodiment, i is between 0.8 and 1.5.

In one embodiment, the polysaccharide is predominantly composed of monomers bonded via glycoside bonds of (1,6) type.

In one embodiment, the polysaccharide predominantly composed of monomers bonded via glycoside bonds of (1,6) type is dextran.

In one embodiment, the polysaccharide is predominantly composed of monomers bonded via glycoside bonds of (1,4) type.

In one embodiment, the polysaccharide predominantly composed of monomers bonded via glycoside bonds of (1,4) type is chosen from the group consisting of pullulan, alginate, hyaluronan, xylan, galacturonan and a water-soluble cellulose.

in one embodiment, the polysaccharide is a pullulan.
In one embodiment, the polysaccharide is an alginate.
In one embodiment, the polysaccharide is a hyaluronan.
In one embodiment, the polysaccharide is a xylan.
In one embodiment, the polysaccharide is a galacturonan.
In one embodiment, the polysaccharide is a water-soluble cellulose.

In one embodiment, the polysaccharide is predominantly composed of monomers bonded via glycoside bonds of (1,3) type.

In one embodiment, the polysaccharide predominantly composed of monomers bonded via glycoside bonds of (1,3) type is a curdlan.

In one embodiment, the polysaccharide is predominantly composed of monomers bonded via glycoside bonds of (1,2) type.

In one embodiment, the polysaccharide predominantly composed of monomers bonded via glycoside bonds of (1,2) type is an inulin.

In one embodiment, the polysaccharide is predominantly composed of monomers bonded via glycoside bonds of (1,4) and (1,3) type.

In one embodiment, the polysaccharide predominantly composed of monomers bonded via glycoside bonds of (1,4) and (1,3) type is a glucan.

In one embodiment, the polysaccharide is predominantly composed of monomers bonded via glycoside bonds of (1,4) and (1,3) and (1,2) type.

In one embodiment, the polysaccharide predominantly composed of monomers bonded via glycoside bonds of (1,4) and (1,3) and (1,2) type is mannan.

In one embodiment, the polysaccharide according to the invention is characterized in that the L-Q sequence is chosen from the group consisting of the following sequences, L having the meaning given above:

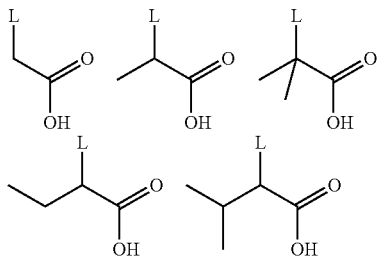

In one embodiment, the polysaccharide according to the invention is characterized in that the L-Q sequence is chosen from the group consisting of the following sequences, L having the meaning given above:

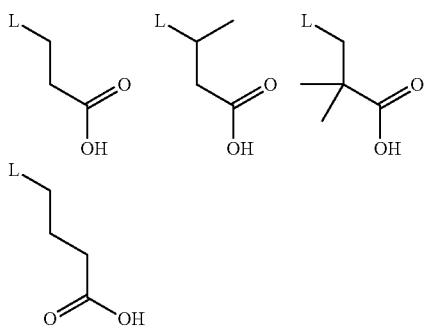

In one embodiment, the polysaccharide according to the invention is characterized in that the L-Q sequence is chosen from the group consisting of the following sequences, L having the meaning given above:

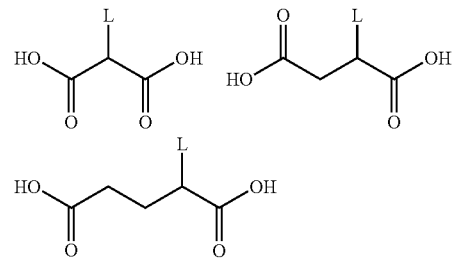

In one embodiment, the polysaccharide according to the invention is characterized in that the precursor of Q is chosen from the group of the amino acids consisting of alanine, leucine, isoleucine, phenylalanine, valine and glycine.

In one embodiment, said anionic polysaccharide monofunctionalized by a hydrophobic acid derivative is chosen from the polysaccharides comprising carboxyl functions of general formula V:

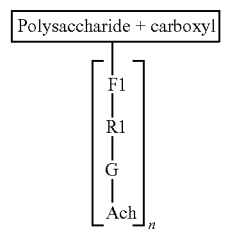

Formula V in which n represents the degree of functionalization of the carboxyl functions of the polysaccharide by an $F_1$—$R_1$-G-Ach sequence and is between 0.01 and 0.7, $F_1$ being either an amide function or an ester function or a thioester function, G being either an ester function or an amide function or a thioester function, $R_1$ being a divalent radical composed of a chain comprising between 1 and 15 carbon atoms which is optionally branched and/or unsaturated, which optionally comprises one or more heteroatoms, such as O, N and/or S, and which optionally comprises one or more saturated, unsaturated or aromatic rings or heterocycles and resulting from the reaction of a precursor $R_1'$ having at least two identical or different reactive functions chosen from the group consisting of alcohol, amine and thiol function, Ach being a radical which is the product of the coupling between the carboxyl function of the hydrophobic acid and at least one reactive functional group carried by the precursor $R_1'$ of the divalent radical $R_1$, and, when the carboxyl function of the polysaccharide is not functionalized by $F_1$—$R_1$-G-Ach, then the carboxyl function or functions of the polysaccharide are cation carboxylates, the cation preferably being that of an alkali metal, such as $Na^+$ or $K^+$.

In one embodiment, $F_1$ is an amide function, G is an ester function, $R_1'$ is an alcohol amine and Ach results from a hydrophobic acid.

In one embodiment, $F_1$ is an amide function, G is a thioester function, $R_1'$ is an aminothioalcohol and Ach results from a hydrophobic acid.

In one embodiment, $F_1$ is an amide function, G is an amide function, $R_1'$ is a diamine and Ach results from a hydrophobic acid.

In one embodiment, $F_1$ is an ester function, G is an amide function, $R_1'$ is an alcohol amine and Ach results from a hydrophobic acid.

In one embodiment, $F_1$ is an ester function, G is an ester function, $R_1'$ is a dialcohol and Ach results from a hydrophobic acid.

In one embodiment, $F_1$ is an ester function, G is a thioester function, $R_1'$ is a hydroxythioalcohol and Ach results from a hydrophobic acid.

In one embodiment, $F_1$ is a thioester function, G is an amide function, $R_1'$ is an aminothioalcohol and Ach results from a hydrophobic acid.

In one embodiment, $F_1$ is a thioester function, G is an ester function, $R_1'$ is a hydroxythioalcohol and Ach results from a hydrophobic acid.

In one embodiment, $F_1$ is a thioester function, G is a thioester function, $R_1'$ is a dithioalcohol and Ach results from a hydrophobic acid.

In one embodiment, said anionic polysaccharide monofunctionalized by a hydrophobic acid derivative is chosen from the polysaccharides comprising carboxyl functions of general formula VI:

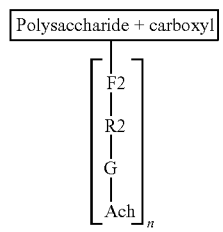

Formula VI in which n represents the degree of functionalization of the hydroxyl functions of the polysaccharide by an $F_2$—$R_2$-G-Ach sequence and is between 0.01 and 0.7, $F_2$ being a carbamate function, G being either an ester function or an amide function or a thioester function, $R_2$ being a divalent radical composed of a chain comprising between 1 and 15 carbons which is optionally branched and/or unsaturated, which optionally comprises one or more heteroatoms, such as O, N and/or S, and which optionally comprises one or more saturated, unsaturated or aromatic rings or heterocycles and resulting from the reaction of a precursor $R_2'$ having at least two reactive functions, one being an amine function and the other being chosen from the group consisting of alcohol, amine and thiol functions, Ach being a radical which is a product of the coupling between the carboxyl function of the hydrophobic acid and at least one reactive function carried by the precursor $R_2'$ of the divalent radical $R_2$, and the carboxyl functions of the polysaccharide being in the form of cation carboxylates, the cation preferably being that of an alkali metal, such as $Na^+$ or $K^+$.

In one embodiment, $F_2$ is a carbamate function, G is an ester function, $R_2'$ is an alcohol amine and Ach results from a hydrophobic acid.

In one embodiment, $F_2$ is a carbamate function, G is a thioester function, $R_2'$ is an aminothioalcohol and Ach results from a hydrophobic acid.

In one embodiment, $F_2$ is a carbamate function, G is an amide function, $R_2'$ is a diamine and Ach results from a hydrophobic acid.

In one embodiment, the precursor of the group $R_1$, $R_1'$, is chosen from dialcohols.

In one embodiment, the dialcohols are chosen from the group consisting of glycerol, diglycerol and triglycerol.

In one embodiment, the dialcohol is triethanolamine.

In one embodiment, the dialcohols are chosen from the group consisting of diethylene glycol and triethylene glycol.

In one embodiment, the dialcohols are chosen from the group consisting of polyethylene glycols.

In one embodiment, the precursors of the groups $R_1$ and $R_2$, $R_1'$ and $R_2'$, are chosen from diamines.

In one embodiment, the diamines are chosen from the group consisting of ethylenediamine and lysine and its derivatives.

In one embodiment, the diamines are chosen from the group consisting of diethylene glycol diamine and triethylene glycol diamine.

In one embodiment, the precursors of the groups $R_1$ and $R_2$, $R_1'$ and $R_2'$, are chosen from alcohol amines.

In one embodiment, the alcohol amines are chosen from the group consisting of ethanolamine, amino-2-propanol, isopropanolamine, 3-amino-1,2-propanediol, diethanolamine, diisopropanolamine, tromethamine (Tris) and 2-(2-aminoethoxy)ethanol.

In one embodiment, the alcohol amines are chosen from the group consisting of reduced amino acids.

In one embodiment, the reduced amino acids are chosen from the group consisting of alaminol, valinol, leucinol, isoleucinol, prolinol and phenylalaminol.

In one embodiment, the alcohol amines are chosen from the group consisting of charged amino acids.

In one embodiment, the charged amino acids are chosen from the group consisting of serine and threonine.

In one embodiment, the hydrophobic acid is chosen from fatty acids.

In one embodiment, the fatty acids are chosen from the group consisting of the acids composed of a saturated or unsaturated and branched or unbranched alkyl chain comprising from 6 to 50 carbon atoms.

In one embodiment, the fatty acids are chosen from the group consisting of linear fatty acids.

In one embodiment, the linear fatty acids are chosen from the group consisting of caproic acid, oenanthic acid, caprylic acid, capric acid, nonanoic acid, decanoic acid, undecanoic acid, dodecanoic acid, palmitic acid, stearic acid, arachidic acid, behenic acid, tricosanoic acid, lignoceric acid, heptacosanoic acid, octacosanoic acid and melissic acid.

In one embodiment, the fatty acids are chosen from the group consisting of unsaturated fatty acids.

In one embodiment, the unsaturated fatty acids are chosen from the group consisting of myristoleic acid, palmitoleic acid, oleic acid, elaidic acid, linoleic acid, alpha-linoleic acid, arachidonic acid, eicosapentaenoic acid, erucic acid and docosahexaenoic acid.

In one embodiment, the fatty acids are chosen from the group consisting of bile acids and their derivatives.

In one embodiment, the bile acids and their derivatives are chosen from the group consisting of cholic acid, dehydrocholic acid, deoxycholic acid and chenodeoxycholic acid.

The polysaccharide can have a degree of polymerization m of between 5 and 10 000.

In one embodiment, it has a degree of polymerization m of between 10 and 1000.

In another embodiment, it has a degree of polymerization m of between 10 and 500.

The invention also relates to the synthesis of the polysaccharides according to the invention.

When the polysaccharides are chosen from the polysaccharides of general formula V, said synthesis comprises a step of producing an aminated intermediate Ach-G-R$_1$—NH$_2$ or an ammonium salt Ach-G-R$_1$—NH$_3^+$, the counterion of which is an anion chosen from halides, sulfates, sulfonates or carboxylates, and a step of grafting this aminated intermediate to a carboxyl function of a polysaccharide, R$_1$, G and Ach corresponding to the definitions given above.

In one embodiment, a step of conversion of the hydroxyls of the polysaccharide to at least 15 carboxyl functions per 100 saccharide units is carried out by grafting compounds of formula Q-L' to at least 15 hydroxyl functions per 100 saccharide units of the polysaccharide, Q-L' being a precursor of the sequence Q-L, Q and L corresponding to the definitions given above.

In a preferred embodiment, the aminated intermediate of formula Ach-G-R$_1$—NH$_2$ or Ach-G-R$_1$—NH$_3^+$ is obtained by reaction of a compound of formula G'-R$_1$—NH$_2$, G' being an amine, thiol or alcohol function, with the acid function of the hydrophobic acid, R$_1$, G and Ach corresponding to the definitions given above.

If necessary, in this step of producing the aminated intermediate, the protection or deprotection techniques well known to a person skilled in the art of peptide synthesis are used.

Preferably, the step of grafting the aminated intermediate to an acid function of the polysaccharide is carried out in an organic medium.

When the polysaccharides are chosen from the polysaccharides of general formula VI, said synthesis comprises a step of producing an aminated intermediate Ach-G-R$_2$—NH$_2$ or an ammonium salt Ach-G-R$_2$—NH$_3^+$, the counterion of which is an anion chosen from halides, sulfates, sulfonates or carboxylates, and a step of grafting this aminated intermediate to a hydroxyl function of a polysaccharide, R$_2$, G and Ach corresponding to the definitions given above.

In a preferred embodiment, the aminated intermediate of formula Ach-G-R$_2$—NH$_2$ or Ach-G-R$_2$—NH$_3^+$ is produced by reaction of a compound of formula G'—R$_2$—NH$_2$, G' being an amine, thiol or alcohol function, with the acid function of the hydrophobic acid, R$_2$, G and Ach corresponding to the definitions given above.

If necessary, in this step of producing the aminated intermediate, the protection or deprotection techniques well known to a person skilled in the art of peptide synthesis are used.

Preferably, the step of grafting the aminated intermediate to a hydroxyl function of the polysaccharide is carried out in an organic medium.

In one embodiment, the invention relates to a polysaccharide chosen from the group consisting of the following polysaccharides:

sodium dextranmethylcarboxylate modified by ethanolamine caprylate ester sodium dextranmethylcarboxylate modified by ethanolamine laurate ester (dextran 40 kDa)

sodium dextranmethylcarboxylate modified by ethanolamine laurate ester (dextran 10 kDa)

sodium dextranmethylcarboxylate modified by phenylalaninol caprylate ester sodium dextranmethylcarboxylate modified by N-(2-aminoethyl)octanamide sodium dextranmethylcarboxylate modified by N-(2-aminoethyl)decanamide sodium dextranmethylcarboxylate modified by N-(2-aminoethyl)dodecanamide (dextran 10 kDa)

sodium dextranmethylcarboxylate modified by N-(2-aminoethyl)dodecanamide (dextran 40 kDa)

sodium dextranmethylcarboxylate modified by 2-(2-[dodecanoylamino]ethoxy)ethylamine sodium dextranmethylcarboxylate modified by 2-(2-{2-[dodecanoylamino]ethoxy}ethoxy)ethylamine sodium dextranmethylcarboxylate modified by 2-(2-{2-[hexadecanoylamino]ethoxy}ethoxy)ethylamine sodium dextranmethylcarboxylate modified by 2-(2-aminoethoxy)ethyl octanoate sodium dextranmethylcarboxylate modified by 2-(2-aminoethoxy)ethyl dodecanoate sodium dextranmethylcarboxylate modified by 2-(2-aminoethoxy)ethyl hexadecanoate sodium dextranmethylcarboxylate modified by 2-[(2-octanoylamino-3-phenyl)propanoylamino]ethanamine sodium dextranmethylcarboxylate modified by 2-[(2-octanoylamino-3-phenyl)propanoylamino]ethanamine N-(sodium methylcarboxylate) dextran carbamate modified by N-(2-aminoethyl)dodecanamide sodium dextransuccinate modified by N-(2-aminoethyl) dodecanamide dextran modified by N-(sodium methylcarboxylate) carbamate and N-(2-aminoethyl)dodecanamide carbamate.

The invention also relates to the use of the functionalized polysaccharides according to the invention in the preparation of pharmaceutical compositions.

The invention also relates to a pharmaceutical composition comprising one of the polysaccharides according to the invention as described above and at least one active principle.

The invention also relates to a pharmaceutical composition, wherein the active principle is chosen from the group consisting of proteins, glycoproteins, peptides and nonpeptide therapeutic molecules.

The term "active principle" is understood to mean a product in the form of a single chemical entity or in the form of a combination having a physiological activity. Said active principle can be exogenous, that is to say that it is introduced by the composition according to the invention. It can also be endogenous, for example the growth factors which will be secreted in a wound during the first phase of healing and which can be retained on said wound by the composition according to the invention.

Depending on the pathologies targeted, it is intended for a local or systemic treatment.

In the case of local and systemic releases, the methods of administration envisaged are by the intravenous, subcutaneous, intradermal, transdermal, intramuscular, oral, nasal, vaginal, occular, buccal or pulmonary routes, and the like.

The pharmaceutical compositions according to the invention are either in the liquid form, in aqueous solution, or in a powder, implant or film form. They additionally comprise the conventional pharmaceutical excipients well known to a person skilled in the art.

Depending on the pathologies and methods of administration, the pharmaceutical compositions can advantageously comprise, in addition, excipients which make it possible to formulate them in the form of a gel, sponge, injectable solution, solution to be taken orally, lyophilized tablet, and the like.

The invention also relates to a pharmaceutical composition, which can be administered in the form of a stent, of a film or coating of implantable biomaterials, or of an implant.

EXAMPLE 1

Sodium Dextranmethylcarboxylate Modified by Ethanolamine Caprylate Ester

Polymer 1

8 g (i.e., 148 mmol of hydroxyl functions) of dextran with a weight-average molar mass of approximately 40 kg/mol (Pharmacosmos) are solubilized in water at 42 g/l. 15 ml of 10N NaOH (148 mmol of NaOH) are added to this solution. The mixture is brought to 35° C. and then 23 g (198 mmol) of sodium chloroacetate are added. The temperature of the reaction medium is brought to 60° C. at 0.5° C./min and then maintained at 60° C. for 100 minutes. The reaction medium is diluted with 200 ml of water, neutralized with acetic acid and purified by ultrafiltration through a 5 kD PES membrane against 6 volumes of water. The final solution is quantitatively determined by dry extract, in order to determine the concentration of polymer, and then quantitatively determined by acid/base titration in 50/50 (v/v) water/acetone, in order to determine the degree of conversion of hydroxyl functions to methylcarboxylates.

According to the dry extract: [polymer]=31.5 mg/g

According to the acid/base titration: the degree of conversion of hydroxyl functions to methylcarboxylate functions is 1.06 per saccharide unit.

The sodium dextranmethylcarboxylate solution is passed over a Purolite resin (anionic) in order to obtain the dextranmethylcarboxylic acid, which is subsequently lyophilized for 18 hours.

Ethanolamine caprylate ester, para-toluenesulfonic acid salt, is obtained according to the process described in the patent (Kenji, M. et al., U.S. Pat. No. 4,826,818).

7.5 g of dextranmethylcarboxylic acid (35.57 mmol of methylcarboxylic acid function) are dissolved in DMF at 60 g/l and then cooled to 0° C. 2.41 g of ethanolamine caprylate ester, para-toluenesulfonic acid salt (6.71 mmol) are suspended in DMF at 100 g/l. 0.68 g of triethylamine (6.71 mmol) is subsequently added to this suspension. Once the polymer solution is at 0° C., a solution of NMM (3.96 g, 39.1 mmol) in DMF (530 g/l) and 4.25 g (39.1 mmol) of EtOCOCl are subsequently added. After reacting for 10 minutes, the ethanolamine caprylate ester suspension is added. The medium is subsequently maintained at 10° C. for 45 minutes. The medium is subsequently heated to 50° C.

An imidazole solution (7.9 g in 13 ml of water) and 39 ml of water are added to the reaction medium. The polymer solution is ultrafiltered through a 10 kD PES membrane against 6 volumes of 0.9% NaCl solution, 3 volumes of 0.01N sodium hydroxide solution, 7 volumes of 0.9% NaCl solution and then 3 volumes of water. The concentration of the polymer solution is determined by dry extract. A fraction of solution is lyophilized and analyzed by $^1$H NMR in $O_2O$ in order to determine the rate of acid functions converted to ethanolamine caprylate ester amide.

According to the dry extract: [polymer 1]=29.1 mg/g

According to the $^1$H NMR: the degree of functionalization of the acids by the ethanolamine caprylate per saccharide unit is 0.15.

EXAMPLE 2

Sodium Dextranmethylcarboxylate Modified by Ethanolamine Laurate Ester (Dextran 40 kDa)

Polymer 2

Ethanolamine laurate ester, para-toluenesulfonic acid salt, is obtained according to the process described in the patent (Kenji, M. et al., U.S. Pat. No. 4,826,818).

A sodium dextranmethylcarboxylate modified by ethanolamine laurate ester is obtained by a process similar to that described in example 1.

According to the dry extract: [polymer 2]=21.2 mg/g

According to the $^1$H NMR: the degree of functionalization of the acids by ethanolamine laurate ester per saccharide unit is 0.09.

EXAMPLE 3

Sodium Dextranmethylcarboxylate Modified by Ethanolamine Laurate Ester (Dextran 10 KDa)

Polymer 3

A sodium dextranmethylcarboxylate synthesized according to the process described in example 1 using a dextran with a weight-average molecular weight of approximately 10 kg/mol (Pharmacosmos), modified by ethanolamine laurate ester by a process similar to that described in example 2 is obtained.

According to the dry extract: [polymer 3]=31.4 mg/g

According to the $^1$H NMR: the degree of functionalization of the acids by ethanolamine laurate ester per saccharide unit is 0.09.

EXAMPLE 4

Sodium Dextranmethylcarboxylate Modified by Phenylalaminol Caprylate Ester

Polymer 4

Phenylalaminol caprylate ester, para-toluenesulfonic acid salt, is obtained according to the process described in the patent (Kenji, M. et al., U.S. Pat. No. 4,826,818).

A sodium dextranmethylcarboxylate modified by phenylalaninol caprylate ester is obtained by a process similar to that described in example 1.

According to the dry extract: [polymer 4]=25 mg/g

According to the $^1$H NMR: the degree of functionalization of the acids by phenylalaminol caprylate ester per saccharide unit is 0.045.

EXAMPLE 5

Sodium dextranmethylcarboxylate modified by N-(2-aminoethyl)octanamide

Polymer 5

N-(2-Aminoethyl)octanamide is obtained according to the process described in the patent (Weiner, N. et al., U.S. Pat. No. 2,387,201) starting from octanoic acid methyl ester (Sigma) and ethylenediamine (Roth).

A dextranmethylcarboxylic acid lyophilizate is obtained from a dextran with a weight-average molar mass of approximately 10 kg/mol (Pharmacosmos) by a process similar to that described in example 1.

8 g of dextranmethylcarboxylic acid (37 mmol of methylcarboxylic acid functions) are solubilized in DMF at 70 g/l and then cooled to 0° C. Once the polymer solution is at 0° C., 4.13 g (41 mmol) of NMM and 4.44 g (41 mmol) of EtOCOCl are subsequently added. After reacting for 10 min, 1.34 g of N-(2-aminoethyl)octanamide (9.0 mmol) are introduced and the medium is brought to 30° C. over 90 minutes. A 600 g/l aqueous imidazole solution and 40 ml of water are added and the medium is subsequently heated to 50° C. The solution obtained is ultrafiltered through a 10 kD PES membrane against 6 volumes of 0.9% NaCl solution, 3 volumes of 0.01N sodium hydroxide solution, 9 volumes of 0.9% NaCl solution and then 3 volumes of water. The concentration of the polymer solution is determined by dry extract. A fraction of solution is lyophilized and analyzed by $^1$H NMR in $D_2O$ in order to determine the rate of acid functions converted to N-(2-aminoethyl)octanamide amide.

According to the dry extract: [polymer 5]=24.8 mg/g

According to the $^1$H NMR: the degree of functionalization of the acids by N-(2-aminoethyl)octanamide per saccharide unit is 0.20.

EXAMPLE 6

Sodium dextranmethylcarboxylate modified by N-(2-aminoethyl)decanamide

Polymer 6

N-(2-Aminoethyl)decanamide is obtained according to the process described in the patent (Weiner, N. et al., U.S. Pat. No. 2,387,201) starting from decanoic acid methyl ester (Sigma) and ethylenediamine (Roth).

A sodium dextranmethylcarboxylate with a weight-average molar mass of 10 kDa modified by N-(2-aminoethyl) decanamide is obtained by a process similar to that described in example 5.

According to the dry extract: [polymer 6]=23.0 mg/g

According to the $^1$H NMR: the degree of functionalization of the acids by N-(2-aminoethyl)decanamide per saccharide unit is 0.09.

EXAMPLE 7

Sodium dextranmethylcarboxylate modified by N-(2-aminoethyl)dodecanamide (dextran 10 kDa)

Polymer 7

N-(2-Aminoethyl)dodecanamide is obtained according to the process described in the patent (Weiner, N. et al., U.S. Pat. No. 2,387,201) starting from dodecanoic acid methyl ester (Sigma) and ethylenediamine (Roth).

A sodium dextranmethylcarboxylate with a weight-average molar mass of 10 kDa modified by N-(2-aminoethyl) dodecanamide is obtained by a process similar to that described in example 5.

According to the dry extract: [polymer 7]=23.8 mg/g

According to the $^1$H NMR: the degree of functionalization of the acids by N-(2-aminoethyl)dodecanamide per saccharide unit is 0.10.

EXAMPLE 8

Sodium dextranmethylcarboxylate modified by N-(2-aminoethyl)dodecanamide (dextran 40 kDa)

Polymer 8

A sodium dextranmethylcarboxylate with a weight-average molar mass of 40 kDa modified by N-(2-aminoethyl) dodecanamide is obtained by a process similar to that described in example 7.

According to the dry extract: [polymer 8]=24.6 mg/g.

According to the $^1$H NMR: the degree of functionalization of the acids by N-(2-aminoethyl)dodecanamide per saccharide unit is 0.10.

EXAMPLE 9

Sodium dextranmethylcarboxylate modified by 2-(2-[dodecanoylamino]ethoxy)ethylaminePolymer 9

2-(2-[Dodecanoylamino]ethoxy)ethylamine is obtained according to the process described in the patent (Weiner, N. et al., U.S. Pat. No. 2,387,201) starting from dodecanoic acid methyl ester (Sigma) and diethylene glycol diamine (Huntsman).

A sodium dextranmethylcarboxylate with a weight-average molar mass of 10 kDa modified by 2-(2-[dodecanoylamino]ethoxy)ethylamine is obtained by a process similar to that described in example 5.

According to the dry extract: [polymer 9]=21.4 mg/g

According to the $^1$H NMR: the degree of functionalization of the acids by 2-(2-[dodecanoylamino]ethoxy)ethylamine per saccharide unit is 0.09.

EXAMPLE 10

Sodium dextranmethylcarboxylate modified by 2-(2-{2-[dodecanoylamino]ethoxy}ethoxy)ethylamine Polymer 10

2-(2-{2-[Dodecanoylamino]ethoxy}ethoxy)ethylamine is obtained according to the process described in the patent (Weiner, N. et al., U.S. Pat. No. 2,387,201) starting from dodecanoic acid methyl ester (Sigma) and triethylene glycol diamine (Huntsman).

A sodium dextranmethylcarboxylate with a weight-average molar mass of 10 kDa modified by 2-(2-{2-[dodecanoylamino]ethoxy}ethoxy)ethylamine is obtained by a process similar to that described in example 5.

According to the dry extract: [polymer 10]=24.9 mg/g

According to the $^1$H NMR: the degree of functionalization of the acids by 2-(2-{2-[dodecanoylamino]ethoxy}ethoxy) ethylamine per saccharide unit is 0.09.

EXAMPLE 11

Sodium dextranmethylcarboxylate modified by 2-(2-{2-[hexadecanoylamino]ethoxy}ethoxy)ethylamine Polymer 11

2-(2-{2-[Hexadecanoylamino]ethoxy}ethoxy)ethylamine is obtained according to the process described in the patent (Weiner, N. et al., U.S. Pat. No. 2,387,201) starting from palmitic acid methyl ester (Sigma) and triethylene glycol diamine (Huntsman).

A sodium dextranmethylcarboxylate with a weight-average molar mass of 10 kDa modified by 2-(2-{2-[hexadecanoylamino]ethoxy}ethoxy)ethylamine is obtained by a process similar to that described in example 5.

According to the dry extract: [polymer 11]=22.2 mg/g

According to the $^1$H NMR: the degree of functionalization of the acids by 2-(2-{2-[hexadecanoylamino] ethoxy}ethoxy)ethylamine per saccharide unit is 0.04.

EXAMPLE 12

Sodium dextranmethylcarboxylate modified by 2-(2-aminoethoxy)ethyl octanoate Polymer 12

2-(2-Aminoethoxy)ethyl octanoate, paratoluenesulfonic acid salt, is obtained according to the process described in the patent (Kenji, M. et al., U.S. Pat. No. 4,826,818) starting from octanoic acid (Sigma) and diethylene glycol amine (Sigma).

A sodium dextranmethylcarboxylate with a weight average molar mass of 10 kDa modified by 2-(2-aminoethoxy)ethyl octanoate is obtained by a process similar to that described in example 1.

According to the dry extract: [polymer 12]=20.3 mg/g

According to the $^1$H NMR: the degree of functionalization of the acids by 2-(2-aminoethoxy)ethyl octanoate per saccharide unit is 0.19.

EXAMPLE 13

Sodium dextranmethylcarboxylate modified by 2-(2-aminoethoxy)ethyl dodecanoate Polymer 13

2-(2-Aminoethoxy)ethyl dodecanoate, paratoluenesulfonic acid salt, is obtained according to the process described in the patent (Kenji, M. et al., U.S. Pat. No. 4,826,818) starting from dodecanoic acid (Sigma) and diethylene glycol amine (Sigma).

A sodium dextranmethylcarboxylate with a weight-average molar mass of 10 kDa modified by 2-(2-aminoethoxy)ethyl dodecanoate is obtained by a process similar to that described in example 1.

According to the dry extract: [polymer 13]=25.6 mg/g

According to the $^1$H NMR: the degree of functionalization of the acids by 2-(2-aminoethoxy)ethyl dodecanoate per saccharide unit is 0.10.

EXAMPLE 14

Sodium dextranmethylcarboxylate modified by 2-(2-aminoethoxy)ethyl hexadecanoate Polymer 14

2-(2-Aminoethoxy)ethyl hexadecanoate, paratoluenesulfonic acid salt, is obtained according to the process described in the patent (Kenji, M. et al., U.S. Pat. No. 4,826,818) starting from hexadecanoic acid (Sigma) and diethylene glycol amine (Sigma).

A sodium dextranmethylcarboxylate with a weight-average molar mass of 10 kDa modified by 2-(2-aminoethoxy)ethyl hexadecanoate is obtained by a process similar to that described in example 1.

According to the dry extract: [polymer 14]=19.6 mg/g

According to $^1$H NMR: the degree of functionalization of the acids by 2-(2-aminoethoxy)ethyl hexadecanoate per saccharide unit is 0.05.

EXAMPLE 15

Sodium dextranmethylcarboxylate modified by 2-[(2-octanoylamino-3-phenyl)propanoylamino] ethanamine Polymer 15

N-Octanoylphenylalanine is obtained according to the process described in the publication (Pal, A. et al., Tetrahedron, 2007, 63, 7334-7348) starting from L-phenylalanine ethyl ester, hydrochloric acid salt, (Bachem) and caprylic acid (Sigma).

2-[(2-Octanoylamino-3-phenyl)propanoylamino]ethanamine, hydrochloric acid salt, is obtained according to the processes described in the publications (Paul, R. et al., J. Org. Chem., 1962, 27, 2094-2099, and Dale, D. J. et al., Org. Process. Res. Dev., 2002, 6, 767-772) starting from N-octanoylphenylalanine and ethylenediamine (Roth).

A sodium dextranmethylcarboxylate with a weight-average molar mass of 10 kDa modified by 2-[(2-octanoylamino-3-phenyl)propanoylamino]ethanamine is obtained by a process similar to that described in example 5.

According to the dry extract: [polymer 15]=19.9 mg/g

According to the $^1$H NMR: the degree of functionalization of the acids by 2-[(2-octanoylamino-3-phenylpropanoyl)amino]ethanamine per saccharide unit is 0.13.

EXAMPLE 16

Sodium dextranmethylcarboxylate modified by 2-[(2-octanoylamino-3-phenyl)propanoylamino] ethanamine Polymer 16

N-Octanoylphenylalanine is obtained according to the process described in the publication (Pal, A. et al., Tetrahedron, 2007, 63, 7334-7348) starting from L-phenylalanine ethyl ester, hydrochloric acid salt, (Bachem) and caprylic acid (Sigma).

2-[(2-Octanoylamino-3-phenyl)propanoylamino]ethanamine, hydrochloric acid salt, is obtained according to the processes described in the publications (Paul, R. et al., J. Org. Chem., 1962, 27, 2094-2099, and Dale, D J, et al., Org. Process. Res. Dev., 2002, 6, 767-772) starting from N-octanoylphenylalanine and ethylenediamine (Roth).

A sodium dextranmethylcarboxylate with a weight-average molar mass of 40 kDa modified by 2-[(2-octanoylamino-3-phenyl)propanoylamino]ethanamine is obtained by a process similar to that described in example 5.

According to the dry extract: [polymer 16]=19.1 mg/g

According to the $^1$H NMR: the degree of functionalization of the acids by 2-[(2-octanoylamino-3-phenyl)propanoylamino]ethanamine per saccharide unit is 0.15.

EXAMPLE 17

N-(Sodium methylcarboxylate) dextran carbamate modified by N-(2-aminoethyl)dodecanamide Polymer 17

N-(2-Aminoethyl)dodecanamide is obtained according to the process described in the patent (Weiner, N. et al., U.S. Pat. No. 2,387,201) starting from dodecanoic acid methyl ester (Sigma) and ethylenediamine (Roth).

11.5 g (i.e., 0.21 mol of hydroxyl functions) of dextran with a weight-average molar mass of approximately 10 kg/mol (Bachem) are solubilized in a DMF/DMSO mixture. The mixture is brought to 130° C. with stirring and 13.75 g (0.11 mol) of ethyl isocyanatoacetate are gradually introduced. After reacting for 1 h, the medium is diluted in water and purified by diafiltration through the 5 kD PES membrane against 0.1N NaOH, 0.9% NaCl and water. The final solution is quantitatively determined by dry extract, in order to determine the concentration of polymer, and then quantitatively determined by acid/base titration in 50/50 (v/v) water-acetone, in order to determine the degree of conversion of the hydroxyl functions to carboxylates.

According to the dry extract: [polymer]=38.9 mg/g

According to the acid/base titration: the degree of conversion of the hydroxyl functions to N-methylcarboxylate carbamate functions is 1.08 per saccharide unit.

The solution of N-(sodium methylcarboxylate) dextran carbamate is passed over a Purolite resin (anionic) in order to obtain the N-(methylcarboxylic acid) dextran carbamate, which is subsequently lyophilized for 18 hours.

5 g of N-(methylcarboxylic acid) dextran carbamate (20 mmol of N-(methylcarboxylic acid) functions) are solubilized in DMF at 50 g/l and then cooled to 0° C. 2.22 g (22 mmol) of NMM and 2.38 g (22 mmol) of EtOCOCl are subsequently added. After reacting for 10 min, 0.45 g (1.8 mmol) of N-(2-aminoethyl)dodecanamide is added and the medium is maintained at 10° C. for 45 minutes. The medium is subsequently heated to 50° C. A 600 g/l aqueous imidazole solution and 25 ml of water are added at 30° C. After stirring at 50° C. for 1 h 30, the solution obtained is ultrafiltered through a 10 kD PES membrane against 0.1 N NaOH, 0.9% NaCl and water. The concentration of the polymer solution is determined by dry extract. A fraction of solution is lyophilized and analyzed by $^1$H NMR in O$_2$O in order to determine the rate of acid functions converted to N-(2-aminoethyl)dodecanamide amide.

According to the dry extract: [polymer 17]=17.8 mg/g

According to the $^1$H NMR: the degree of functionalization of the acids by N-(2-aminoethyl)dodecanamide per saccharide unit is 0.1.

EXAMPLE 18

Sodium dextransuccinate modified by
N-(2-aminoethyl)dodecanamide

Polymer 18

N-(2-Aminoethyl)dodecanamide is obtained according to the process described in the patent (Weiner, N. et al., U.S. Pat. No. 2,387,201) starting from dodecanoic acid methyl ester (Sigma) and ethylenediamine (Roth).

Sodium dextransuccinate is obtained from dextran 10 according to the method described in the paper by Sanchez-Chaves et al. (Sanchez-Chaves, Manuel et al., Polymer, 1998, 39 (13), 2751-2757). The rate of acid functions per glycoside unit is 1.41 according to the $^1$H NMR in D$_2$O/NaOD.

A sodium dextransuccinate modified by N-(2-aminoethyl)dodecanamide is obtained by a process similar to that described in example 1.

According to the dry extract: [polymer 18]=16.1 mg/g

According to the $^1$H NMR: the degree of functionalization of the acids by N-(2-aminoethyl)dodecanamide per saccharide unit is 0.05.

EXAMPLE 19

Dextran modified by N-(sodium methylcarboxylate) carbamate and N-(2-aminoethyl)dodecanamide carba mate Polymer 19

N-(2-Aminoethyl)dodecanamide is obtained according to the process described in the patent (Weiner, N. et al., U.S. Pat. No. 2,387,201) starting from dodecanoic acid methyl ester (Sigma) and ethylenediamine (Roth).

N-(2-Isocyanatoethyl)dodecanamide is obtained according to the process described in the publication (Knockler, H.-J. et al., Synlett., 1997, 925-928) starting from N-(2-aminoethyl)dodecanamide.

2.7 g (i.e., 0.05 mol of hydroxyl functions) of dextran with a weight-average molar mass of approximately 10 kg/mol (Bachem) are solubilized in a DMF/DMSO mixture. The mixture is brought to 130° C. with stirring and 3.2 g (0.025 mol) of ethyl isocyanatoacetate and then 2.22 g (0.008 mol) of N-(2-isocyanatoethyl)dodecanamide are gradually introduced. After reacting for 1 h, the medium is diluted in water and purified by diafiltration through a 5 kD PES membrane against 0.1 N NaOH, 0.9% NaCl and water. The final solution is quantitatively determined by dry extract, in order to determine the concentration of polymer. A fraction of solution is lyophilized and analyzed by $^1$H NMR in D$_2$O in order to determine the degree of conversion of the hydroxyl functions to N-(sodium methylcarboxylate) carbamate and the degree of functionalization of the hydroxyl functions to give N-(2-aminoethyl)dodecanamide carbamate.

According to the dry extract: [polymer 19]=6.5 mg/g

According to the $^1$H NMR: the degree of conversion of the hydroxyl functions to N-(sodium methylcarboxylate) carbamate is 1.1 and the degree of functionalization of the hydroxyl functions to give N-(2-aminoethyl)dodecanamide carbamate is 0.05.

What is claimed is:

1. An anionic polysaccharide comprising saccharide units including carboxyl functions and being monofunctionalized with a hydrophobic function -M-Ach according to Formula I,

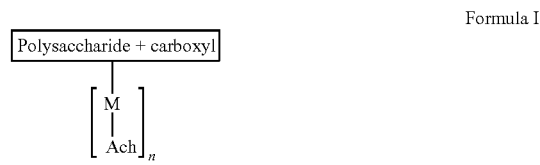

Formula I in which:
n represents the degree of functionalization of the saccharide units by -M-Ach and is between 0.01 and 0.7;
Ach is a hydrophobic radical composed of a chain comprising between 4 and 50 carbons which is optionally branched and/or unsaturated, which optionally comprises one or more heteroatoms, and which optionally comprises one or more saturated, unsaturated or aromatic rings or heterocycles;
M is either —F$_1$—R$_1$-G or —F$_2$-R$_2$-G;
F$_1$ is an amide function, an ester function or a thioester function;
F$_2$ is a carbamate function;
R$_1$ is a divalent radical composed of a chain comprising between 1 and 15 carbons which is optionally branched and/or unsaturated, which optionally comprises one or more heteroatoms, and which optionally comprises one or more saturated, unsaturated or aromatic rings or heterocycles;
R$_2$ is a divalent radical composed of a chain comprising between 1 and 15 carbons which is optionally branched and/or unsaturated, which optionally comprises one or more heteroatoms, and which optionally comprises one or more saturated, unsaturated or aromatic rings or heterocycles; and G is an amide function, an ester function or a thioester function, wherein:
said connecting arm $R_1$ is bonded to the polysaccharide via said bond $F_1$ resulting from the coupling between a reactive function of a precursor of the connecting arm $R_1'$ and a carboxyl function of the anionic polysaccharide and said hydrophobic radical Ach is bonded to the connecting arm $R_1$ via said function G resulting from the coupling between an acid function of a hydrophobic acid and a reactive function of the precursor of the connecting arm $R_1'$;
said connecting arm $R_2$ is bonded to the polysaccharide via said bond $F_2$ resulting from the coupling between a reactive function of a precursor of the connecting arm $R2'$ and a hydroxyl function of the anionic polysaccharide and said hydrophobic radical Ach is bonded to the connecting arm $R_2$ via said function G resulting from the coupling between an acid function of a hydrophobic acid and a reactive function of the precursor of the connecting arm $R_2'$;
the unfunctionalized carboxyl functions of the anionic polysaccharide are in salt form;
Ach results from the coupling between the acid function of the hydrophobic acid and the reactive function of the precursor of the connecting arm $R_1'$ or $R_2'$;
$R_1$ results from the reaction of the precursor $R_1'$ having at least two identical or different reactive functions selected from the group consisting of alcohol, amine and thiol functions; and
$R_2$ results from the reaction of the precursor $R_2'$ having at least two reactive functions, one being an amine and the other being selected from the group consisting of alcohol, amine and thiol functions.

2. The anionic polysaccharide as claimed in claim 1, obtained from a precursor polysaccharide naturally comprising carboxyl functions before functionalization with the hydrophobic function -M-Ach, the precursor polysaccharide being selected from the group consisting of alginate, hyaluronan and galacturonan.

3. The anionic polysaccharide as claimed in claim 1, obtained from a synthetic precursor polysaccharide of Formula II before functionalization with the hydrophobic function -M-Ach, wherein the synthetic precursor polysaccharide is obtained by converting hydroxyl functions to carboxylates in a polysaccharide naturally comprising hydroxyl and carboxyl functions or a neutral polysaccharide naturally comprising hydroxyl functions, for which the degree of conversion of hydroxyl functions to carboxylates per saccharide unit is equal to or greater than 0.15,

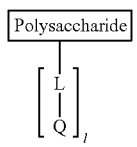

Formula II in which:
the polysaccharide is selected from the group consisting of the polysaccharides predominantly composed of monomers bonded via glycoside bonds of (1,6) and/or (1,4) and/or (1,3) and/or (1,2) type;

L is a bond resulting from the coupling between a precursor of the connecting arm Q and an a hydroxyl function of the polysaccharide and is an ester, carbamate or ether function;
i represents the degree of conversion of the hydroxyl functions to L-Q sequences per saccharide unit of the polysaccharide; and
Q is of Formula III:

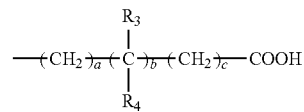

Formula III in which:
$1 \leq a + b + c \leq 6$, $0 \leq a \leq 3$, $0 \leq b \leq 3$ and $0 \leq c \leq 3$; and
$R_3$ and $R_4$, which are identical or different, are selected from the group consisting of —H, linear or branched $C_1$ to $C_3$ alkyl groups, —COOH and the radical of Formula IV,

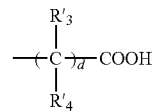

Formula IV in which:
$1 \leq d \leq 3$; and
$R'_3$ and $R'_4$, which are identical or different, are selected from the group consisting of —H and linear or branched $C_1$ to $C_3$ alkyl groups.

4. The anionic polysaccharide as claimed in claim 3, wherein the polysaccharide is predominantly composed of monomers bonded via glycoside bonds of (1,6) type.

5. The anionic polysaccharide as claimed in claim 4, wherein the polysaccharide predominantly composed of monomers bonded via glycoside bonds of (1,6) type is dextran.

6. The anionic polysaccharide as claimed in claim 3, wherein the polysaccharide is predominantly composed of monomers bonded via glycoside bonds of (1,4) type.

7. The anionic polysaccharide as claimed in claim 6, wherein the polysaccharide predominantly composed of monomers bonded via glycoside bonds of (1,4) type is selected from the group consisting of pullulan, alginate, hyaluronan, xylan, galacturonan and a water-soluble cellulose.

8. The anionic polysaccharide as claimed in claim 3, wherein the polysaccharide is predominantly composed of monomers bonded via glycoside bonds of (1,3) type.

9. The anionic polysaccharide as claimed in claim 8, wherein the polysaccharide predominantly composed of monomers bonded via glycoside bonds of (1,3) type is a curdlan.

10. The anionic polysaccharide as claimed in claim 3, wherein the polysaccharide is predominantly composed of monomers bonded via glycoside bonds of (1,2) type.

11. The anionic polysaccharide as claimed in claim 10, wherein the polysaccharide predominantly composed of monomers bonded via glycoside bonds of (1,2) type is an inulin.

12. The anionic polysaccharide as claimed in claim 3, wherein the polysaccharide is predominantly composed of monomers bonded via glycoside bonds of (1,4) and (1,3) type.

13. The anionic polysaccharide as claimed in claim 12, wherein the polysaccharide predominantly composed of monomers bonded via glycoside bonds of (1,4) and (1,3) type is a glucan.

14. The anionic polysaccharide as claimed in claim 3, wherein the polysaccharide is predominantly composed of monomers bonded via glycoside bonds of (1,4) and (1,3) and (1,2) type.

15. The anionic polysaccharide as claimed in claim 14, wherein the polysaccharide predominantly composed of monomers bonded via glycoside bonds of (1,4) and (1,3) and (1,2) type is mannan.

16. The anionic polysaccharide as claimed in claim 3, wherein L-Q is selected from the group consisting of:

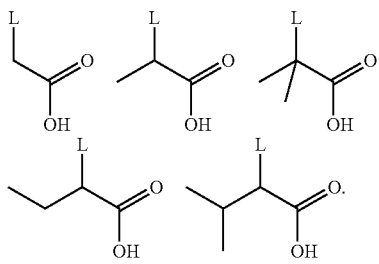

17. The anionic polysaccharide as claimed in claim 3, wherein L-Q is selected from the group consisting of:

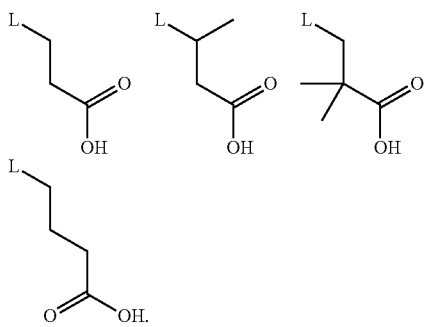

18. The anionic polysaccharide as claimed in claim 3, wherein L-Q is selected from the group consisting of:

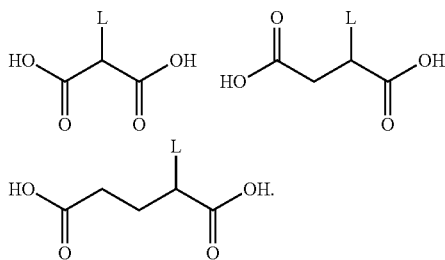

19. The anionic polysaccharide as claimed claim 3, wherein the Q precursor is selected from the group of amino acids consisting of alanine, leucine, isoleucine, phenylalanine, valine and glycine.

20. The anionic polysaccharide as claimed in claim 1, wherein M is —$F_1$—$R_1$-G so that the anionic polysaccharide is of Formula V:

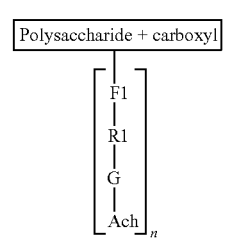

Formula V and any carboxyl function of the polysaccharide that is not functionalized by $F_1$—$R_1$-G-Ach is in salt form.

21. The anionic polysaccharide as claimed in claim 1, wherein M is —$F_2$—$R_2$-G so that the anionic polysaccharide is of Formula VI:

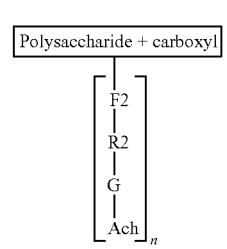

Formula VI and the carboxyl functions of the polysaccharide are in salt form.

22. The anionic polysaccharide as claimed in claim 20, wherein the precursor $R_1'$ is a dialcohol.

23. The anionic polysaccharide as claimed in claim 1, wherein the precursors $R_1'$ and $R_2'$ are diamines.

24. The anionic polysaccharide as claimed in claim 1, wherein the precursors $R_1'$ and $R_2'$ are alcohol amines.

25. The anionic polysaccharide as claimed in claim 1, wherein the hydrophobic acid is a fatty acid.

26. The anionic polysaccharide as claimed in claim 25, wherein the fatty acid is selected from the group consisting of the acids composed of a saturated or unsaturated and branched or unbranched alkyl chain comprising from 6 to 50 carbons.

27. The anionic polysaccharide as claimed in claim 25, wherein the fatty acid is a linear fatty acid.

28. The anionic polysaccharide as claimed in claim 27, wherein the linear fatty acid is selected from the group consisting of caproic acid, oenanthic acid, caprylic acid, capric acid, nonanoic acid, decanoic acid, undecanoic acid, dodecanoic acid, palmitic acid, stearic acid, arachidic acid, behenic acid, tricosanoic acid, lignoceric acid, heptacosanoic acid, octacosanoic acid and melissic acid.

29. The anionic polysaccharide as claimed in claim 25, wherein the fatty acid is an unsaturated fatty acid.

30. The anionic polysaccharide as claimed in claim 29, wherein the unsaturated fatty acid is selected from the group consisting of myristoleic acid, palmitoleic acid, oleic acid, elaidic acid, linoleic acid, alpha-linoleic acid, arachidonic acid, eicosapentaenoic acid, erucic acid and docosahexaenoic acid.

31. The anionic polysaccharide as claimed in claim 25, wherein the fatty acid is a bile acid or a derivative thereof.

32. The anionic polysaccharide as claimed in claim 31, wherein the bile acid or derivative thereof is selected from the group consisting of cholic acid, dehydrocholic acid, deoxycholic acid, chenodeoxycholic acid, and derivatives thereof.

33. The anionic polysaccharide as claimed in claim 1, wherein the degree of polymerization is between 5 and 10 000.

34. The anionic polysaccharide as claimed in claim 1, wherein the degree of polymerization is between 10 and 1000.

35. The anionic polysaccharide as claimed in claim 1, wherein the degree of polymerization is between 10 and 50.

36. A process for the synthesis of the anionic polysaccharide as claimed in claim 20, comprising:
    producing an aminated intermediate Ach-G-$R_1$—$NH_2$ or an ammonium salt Ach-G-$R_1$—$NH_3^+$, the counterion of which is an anion selected from the group consisting of halides, sulfates, sulfonates and carboxylates; and
    grafting the aminated intermediate to a carboxyl function of a polysaccharide.

37. A process for the synthesis of the anionic polysaccharide as claimed in claim 21, comprising:
    producing an aminated intermediate Ach-G-$R_2$—$NH_2$ or an ammonium salt Ach-G-$R_2$—$NH_3^+$, the counterion of which is an anion selected from the group consisting of halides, sulfates, sulfonates and carboxylates; and
    grafting the aminated intermediate to a hydroxyl functional group of a polysaccharide.

38. A pharmaceutical composition comprising the anionic polysaccharide as claimed in claim 1 and at least one active principle.

39. The pharmaceutical composition as claimed in claim 38, formulated to be administered by an oral, nasal, vaginal or buccal route.

40. The pharmaceutical composition as claimed in claim 38, wherein the active principle is selected from the group consisting of proteins, glycoproteins, peptides and nonpeptide therapeutic molecules.

41. The anionic polysaccharide as claimed in claim 1, wherein the unfunctionalized carboxyl functions are in salt form with $Na^+$ or $K^+$.

42. A polysaccharide comprising saccharide units including carboxyl functions and being monofunctionalized with a hydrophobic function -M-Ach according to Formula I,

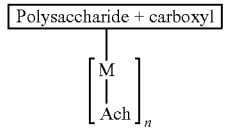

Formula I in which:
    n represents the degree of functionalization of the saccharide units by -M-Ach and is between 0.01 and 0.7;
    Ach is a hydrophobic radical composed of a chain comprising between 4 and 50 carbons which is optionally branched and/or unsaturated, which optionally comprises one or more heteroatoms, and which optionally comprises one or more saturated, unsaturated or aromatic rings or heterocycles;
    M is either —$F_1$—$R_1$-G or —$F_2$—$R_2$-G;
    $F_1$ is an amide function, an ester function or a thioester function that results from functionalization of a carboxyl function of the polysaccharide;
    $F_2$ is a carbamate function that results from functionalization of a hydroxyl group of the polysaccharide;
    $R_1$ is a divalent radical composed of a chain comprising between 1 and 15 carbons which is optionally branched and/or unsaturated, which optionally comprises one or more heteroatoms, and which optionally comprises one or more saturated, unsaturated or aromatic rings or heterocycles;
    $R_2$ is a divalent radical composed of a chain comprising between 1 and 15 carbons which is optionally branched and/or unsaturated, which optionally comprises one or more heteroatoms, and which optionally comprises one or more saturated, unsaturated or aromatic rings or heterocycles; and
    G is an amide function, an ester function or a thioester function that forms a bond with Ach,
    wherein unfunctionalized carboxyl functions of the polysaccharide are in salt form.

43. The polysaccharide as claimed in claim 42, wherein the polysaccharide is selected from the group consisting of:
    sodium dextranmethylcarboxylate modified by ethanolamine caprylate ester;
    sodium dextranmethylcarboxylate modified by ethanolamine laurate ester;
    sodium dextranmethylcarboxylate modified by phenylalaninol caprylate ester;
    sodium dextranmethylcarboxylate modified by N-(2-aminoethyl)octanamide;
    sodium dextranmethylcarboxylate modified by N-(2-aminoethyl)decanamide;
    sodium dextranmethylcarboxylate modified by N-(2-aminoethyl)dodecanamide;
    sodium dextranmethylcarboxylate modified by 2-(2-[dodecanoylamino]ethoxy)ethylamine;
    sodium dextranmethylcarboxylate modified by 2-(2-{2-[dodecanoylamino]ethoxy}ethoxy)ethylamine;
    sodium dextranmethylcarboxylate modified by 2-(2-{2-[hexadecanoylamino] ethoxy}ethoxy)ethylamine;
    sodium dextranmethylcarboxylate modified by 2-(2-aminoethoxy)ethyl octanoate;
    sodium dextranmethylcarboxylate modified by 2-(2-aminoethoxy)ethyl dodecanoate;
    sodium dextranmethylcarboxylate modified by 2-(2-aminoethoxy)ethyl hexadecanoate;
    sodium dextranmethylcarboxylate modified by 2-[(2-octanoylamino-3-phenyl)propanoylamino]ethanamine;
    N-(sodium methylcarboxylate) dextran carbamate modified by N-(2-aminoethyl)dodecanamide;
    sodium dextransuccinate modified by N-(2-aminoethyl) dodecanamide; and
    dextran modified by N-(sodium methylcarboxylate) carbamate and N-(2-aminoethyl)dodecanamide carbamate.

44. The polysaccharide as claimed in claim 42, wherein the polysaccharide is a sodium dextranmethylcarboxylate modified by N-(2-aminoethyl)dodecanamide.

* * * * *